United States Patent
Galle (10) Patent No.: US 8,035,813 B2
(45) Date of Patent: Oct. 11, 2011

(54) METHOD AND DEVICE FOR MEASURING EMISSIONS OF GASEOUS SUBSTANCES TO THE ATMOSPHERE USING SCATTERED SUNLIGHT SPECTROSCOPY

(76) Inventor: Bo Galle, Nossebro (SE)

( * ) Notice: Subject to any disclaimer, the term of this patent is extended or adjusted under 35 U.S.C. 154(b) by 336 days.

(21) Appl. No.: 12/308,548

(22) PCT Filed: Jun. 16, 2006

(86) PCT No.: PCT/SE2006/000738
§ 371 (c)(1),
(2), (4) Date: Dec. 15, 2008

(87) PCT Pub. No.: WO2007/145554
PCT Pub. Date: Dec. 21, 2007

(65) Prior Publication Data
US 2010/0231906 A1    Sep. 16, 2010

(51) Int. Cl.
*G01J 3/28* (2006.01)
(52) U.S. Cl. ........................ 356/326; 356/342
(58) Field of Classification Search ........... 356/326, 356/342, 438; 250/338.5
See application file for complete search history.

(56) References Cited

U.S. PATENT DOCUMENTS

| | | |
|---|---|---|
| 3,528,740 A | 9/1970 | Gerry et al. |
| 3,768,908 A | 10/1973 | Zaromb |
| 3,788,742 A | 1/1974 | Garbuny |
| 3,984,685 A * | 10/1976 | Fletcher et al. ........... 250/339.11 |
| 6,822,742 B1 | 11/2004 | Kalayeh et al. |
| 2006/0132780 A1 * | 6/2006 | Holland et al. ................ 356/419 |

FOREIGN PATENT DOCUMENTS

WO    WO-02/04902 A1    1/2002

OTHER PUBLICATIONS

Galle, et al., "A Miniaturised ultraviolet spectrometer for remote sensing of $SO_2$ fluxes: a new tool for volcano surveillance", Journal of Volcanology and Geothermal Research, vol. 19, pre. 241-254, 2002.
Edmonds, et al., "Automated, high-resolution measurements of $SO_2$ flux at Soufriere Hills Volcano, Montserrat", Bull Volcanol, vol. 65, pp. 578-586, 2003.
McGonigle, et al., "Sulphur dioxide fluxes from Mount Etna, Vulcano, and Stromboli measured with an automated scanning ultraviolet spectrometer", Journal of Geophysical Research, vol. 108, No. B9, EVC 8-1 thru 8-9, 2003.
Galle, et al., "Dual-Beam mini DOAS spectroscopy for volcanic gas emission monitoring", EGU General Assembly, Vienna, 24-129 Apr. 2005.

* cited by examiner

*Primary Examiner* — Kara E Geisel
(74) *Attorney, Agent, or Firm* — Lerner, David, Littenberg, Krumholz & Mentlik, LLP (57) ABSTRACT

Methods for measuring emissions of gaseous substances to the atmosphere using scattered sunlight spectroscopy and an optical measuring device are disclosed in which the device includes a telescopic member defining a field-of-view of the optical measuring device and a scanner for controlling variation of the direction of the field of view to scan a predetermined layer of the atmosphere, the method comprising scanning the field-of-view to scan the predetermined layer of the atmosphere in the form of at least a part of a cone having its apex positioned at the optical measuring device and having a cone angle β. Optical measuring devices themselves are disclosed.

20 Claims, 8 Drawing Sheets

FIG. 1

Prior Art

Prior Art

FIG. 11

METHOD AND DEVICE FOR MEASURING EMISSIONS OF GASEOUS SUBSTANCES TO THE ATMOSPHERE USING SCATTERED SUNLIGHT SPECTROSCOPY

FIELD OF THE INVENTION

The present invention relates to a method for measuring emissions of gaseous substances to the atmosphere using scattered sunlight spectroscopy and an optical measuring device. The present invention also relates to an optical measuring device for use in such a method.

BACKGROUND OF THE INVENTION

Gaseous substances are constantly emitted to the atmosphere from both anthropogenic sources, such as vehicles and industries, and natural sources, such as volcanoes. Many of these substances have an effect on human health and/or on the global climate, the protective ozone layer in the stratosphere or other environmental effects. In order to study such effects and to quantify different sources etc., it is important that there are suitable equipment and methods available for measuring emissions and flux of such gaseous substances. The principles of some different methods are described in e.g. WO 02/04902.

Measurement of gases from volcanoes are important not only for studying their environmental impact and their effect on atmospheric chemistry, but also with regard to geo-science, as the gases emitted from a volcano carry important information on the geophysical and geochemical status of the interior of the volcano, as well as to risk mitigation/assessment, since the gas emission and composition adds to our understanding of the volcanoes status.

In measurements of gases emitted from relatively well demarcated sources, such as discharges from industries and volcanoes, the emissions can be measured at, or at least relatively close to, the source. In such measurements methods based on scattered sunlight spectroscopy are useful. In principle, scattered sunlight spectroscopy involves the use of a spectrometer to record the light of the zenith sky, i.e. the sky straight above the spectrometer, wherein an integration is made over the whole of the cross section of the emitted air mass. This results in a spectrum of the zenith sky including the vertically integrated concentration of the gases which are present in the atmosphere. By moving the spectrometer in such a way that the vertical layer that is measured cuts the emitted gas mass, e.g. an emission plume from a source, it is possible, after geometrical correction for deviations in direction of movement from a direction perpendicular to the propagation of the gas mass and after correcting for background concentration, to determine the integrated concentration over a cross section of the emitted gas mass. The emission is obtained after multiplying this integrated concentration with the concentration-weighed wind speed A scattered sunlight spectroscopy instrument that has been used extensively in studies of volcano emissions is the so-called COSPEC-instrument, which is an optical remote sensing instrument developed in the 70's. It consists of a spectrometer that receives scattered UV-light from a narrow solid angle of the blue sky, typically at zenith. $SO_2$ has a characteristic absorption spectrum around 300 nm. By means of a mask correlation technique the instrument is able to derive the total column of $SO_2$ molecules along the vertical path or column defined by the instruments field-of-view (FOV). Thus the vertically integrated number of $SO_2$ molecules in a segment of a volcanic plume may be derived. By installing the instrument on a moving platform, and move the platform in a direction such that the instruments FOV cuts the volcanic gas plume, the total number of $SO_2$ molecules in a cross-section perpendicular to the direction of propagation of the plume may be derived. Multiplying this number with the molecular weight and the wind-speed gives the mass-flux in kg/s. The COSPEC-instrument has the advantage that the measurements can be made remotely at distances of several km from the source and that mass flux can be derived. For these reasons it has become the most important technique for volcanic gas emission monitoring.

Technological development during the recent decades has resulted in sensitive and fast multi-channel array detectors, powerful computers, and algorithms for modelling of radiative transfer and accurate analysis of differential absorption spectra. This has led to an alternative to the COSPEC-instrument: a miniature fiber optic ultraviolet differential optical absorption spectrometer: the mini-DOAS, which is described in Galle B., Oppenheimer C., Geyer A., McGonigle A., Edmonds M. and Horrocks L., "A miniaturised ultraviolet spectrometer for remote sensing of $SO_2$ fluxes: a new tool for volcano surveillance". *Journal of Volcanology and Geothermal Research*, Volume 119, Issues 1-4, 1 Jan. 2003, Pages 241-254. The basic mini-DOAS system consists of a pointing telescope fiber-coupled to a miniature spectrograph. Ultraviolet light from the sun, scattered from aerosols and molecules in the atmosphere, is collected by means of the telescope (length 10 cm, diameter 3 cm) with a quartz lens defining a field-of-view of 8 mrad. Light is transferred from the telescope to the spectrometer by means of a 2 m long optical quartz fiber with 800 μm diameter. The spectrometer uses a 2400 lines/mm grating combined with a 50 μm slit, providing an optical resolution of ~0.6 nm over a wavelength range of 245-380 nm. The software used for controlling the spectrometer as well as for evaluating the spectra is a custom-built program.

In a typical zenith sky measurement the mini-DOAS is carried by car or foot, and spectra are recorded whilst the instrument is moved under the volcanic gas plume in a direction approximately perpendicular to the plume transport direction. The platform position is tracked using a GPS receiver making it possible to geometrically correct for deviations in movement from the ideal direction perpendicular to the plume transport direction. In this manner the total number of molecules in a thin layer of the plume can be determined, and after multiplication with wind speed at plume height, the mass flow of the emission can be obtained, e.g. in kg/s. Besides being a cost-effective alternative to the COSPEC, the introduction of the mini-DOAS represented a major step forward in terms of field-operability, mobility and flexibility. The small size and power consumption of the device made possible measurements in hitherto inaccessible areas and situations.

The mini-DOAS has been further developed in that the instrument was coupled to a scanning device consisting of a quartz-prism attached to a computer-controlled stepper-motor, providing a means to scan the field-of view of the instrument over 180°, see Edmonds M., R. A. Herd, B. Galle and C. Oppenheimer, "Automated, high time-resolution measurements of $SO_2$ flux at Soufrière Hills Volcano, Montserrat", *Bulletin of Volcanology*, Vol 65, 578-586, 2003. In a typical measurement the instrument is located under the plume, and scans are made, from horizon to horizon, in a plane perpendicular to the wind-direction. Thus, instead of moving the measurement equipment under the gas plume, this version of the mini-DOAS is capable of scanning a plane in the sky from a stationary position. Of course, this feature simplifies the measurement considerably. A stepwise scan of the plane typically use a 10 seconds integration time with 7.5° angular resolution, providing a full emission measurement every 4 minutes. The scanning mini-DOAS provides time resolved measurement of the gas emission, making it possible to correlate gas emission data with other geophysical data, e.g. seismic signals. A similar approach but using a mirror instead of a prism in the scanning device has also been used for volcanic gas measurements, McGonigle A. J. S., C. Oppenheimer, A. R. Hayes, B. Galle, M. Edmonds, T. Caltabiano, G. Salerno and M. Burton, "Volcanic sulphur dioxide flux measurements at Etna, Vulcano and Stromboli obtained using an automated scanning ultraviolet spectrometer", *Journal of Geophysical Research*, vol 108, No B9, 2455, 2003.

As mentioned above one of the main advantages of the scanning mini-DOAS is that it is a stationary instrument that does not have to be moved during the measurement. However, this also means that the emission can only be measured when the wind direction is such that the gas plume from the volcano is passing over the instrument within a certain angular interval around zenith. If the wind direction changes such that it falls outside this interval the gas plume will, at least partly, be intersected by the instruments field-of-view at too high zenith angles to facilitate a good measurement. Typically it will not be able to determine unambiguously the clean air background below the plume. An effect of this is that it becomes difficult to evaluate the integrated concentration in the gas plume which leads to an unreliable determination of the amounts of emissions in the plume. In order to solve this problem efforts have been made to improve the mathematical algorithms for calculating the area of such incomplete plume scans by assuming certain plume dispersion characteristics and applying meteorological dispersion models. Another, more practical way, to solve this problem is to move the instrument or to install a number of instruments around the emission source such that the measurement ranges of two adjacent instruments overlap.

Another problem related to this measurement strategy is caused by scattering of light in the lower part of the atmosphere. In the described measurement strategy it is assumed that all the light that reach the instrument originates from a volume above the gas plume to be studied. If the Sun is located at an angle off zenith, direct light from the Sun may be scattered by aerosols and molecules located between the instrument and the gas plume, into the field-of-view of the instrument. This part of the recorded light has never passed the gas plume and thus causes a "diluted" spectrum, giving rise to an underestimation of the gas content in the plume. This problem gets worse the more aerosols (haze, particles, ash, rain, etc.) there is in the lower atmosphere. It also gets worse when the plume is intersected at high zenith angles (close to the horizon) and when the distance between the instrument and the gas plume is long.

To calculate the emission using the above mentioned methods, a knowledge of the transport speed of the gas plume is necessary. This can be obtained either by meteorological modeling, by extrapolating meteorological measurements made elsewhere or by measurement. A method for measuring the transport speed of the gas plume directly has been developed using DOAS techniques. In this method two DOAS instruments, similar to the systems described above, are located under the gas plume and made to point in two different directions, one beam upwind and the other downwind the plume, along the plume propagation direction. A time series of total column variations are registered in both directions, and from the temporal delay in variations in the total column, the wind-speed can be calculated if the plume height is known. Instead of two separate DOAS instruments one single system may be used where a flipping mirror instead alternates the pointing direction of the system between two directions. Ideally the parameter to be measured is the wind speed at plume height, weighted by plume concentration. As this approach uses variations in the total column of $SO_2$ to determine the plume speed, a weighting with concentration is automatically made. Examples of wind measurements using this approach at Etna Volcano on Sicily and Popocatepetl Volcano in Mexico are given in Galle B., M. Johansson, C. Rivera and Y. Zhang, "*Dual-Beam mini-DOAS spectroscopy, a novel approach for volcanic gas emission monitoring*", EGU General Assembly, Vienna, 24-29 Apr. 2005.

One object of the present invention is to provide a method and a device for measurements of the type described above, which method and device exhibit improved properties compared to conventional instruments and methods, in particular with regard to changing wind directions.

SUMMARY OF THE INVENTION

In accordance with the present invention, this and other objects have now been realized by the discovery of a method for measuring emissions of gaseous substances to the atmosphere using scattered sunlight spectroscopy and an optical measuring device comprising a telescopic member defining a field-of-view of the optical measuring device, and a scanner for controlling the variation of the direction of the field-of-view to scan a predetermined layer of the atmosphere, the method comprising scanning the field-of-view to scan the predetermined layer of the atmosphere in the form of at least a part of a cone having its apex positioned at the optical measuring device and having a cone angle $\beta$. Preferably, the cone angle $\beta$ is up to 80°, more preferably at least 20°. In a preferred embodiment, the angle $\beta$ is from 40 to 70°.

In accordance with another embodiment of the method of the present invention, the cone has its axis of symmetry in a horizontal direction. In another embodiment, the cone has an axis of symmetry exhibiting an inclination angle ($\delta$) relative to a horizontal plane. Preferably, the inclination angle ($\delta$) is $90°-\beta$.

In accordance with the present invention, this and other objects have now been overcome by the discovery of an optical measuring device for measuring emissions of gaseous substances to the atmosphere using scattered sunlight spectroscopy, the device comprising a telescopic member defining a field-of-view of the measuring device, and a scanner for controlling the variation of the direction of the field-of-view to scan a predetermined layer of the atmosphere, the scanner being adapted to scan the predetermined layer of the atmosphere in the form of at least a part of a cone having its apex positioned at the optical measuring device and having a cone angle $\beta$. Preferably, the cone angle $\beta$ is up to 80°, and in another preferred embodiment, the cone angle $\beta$ is at least 20°. In a preferred embodiment, the cone angle $\beta$ is from 40 to 70°. In accordance with another embodiment of the device of the present invention, the scanner comprises a light refracting member arranged to deflect the field-of-view by directing a portion of incoming sunlight towards the telescopic member. Preferably, the light refracting member is arranged in such a way that the non-deflected field-of-view and the deflected field-of-view form the angle $\beta$. In another embodiment, the light refracting member is rotatably arranged in relation to the telescopic member whereby rotation of the light refracting member allows the field-of-view to scan the predetermined layer of the atmosphere. In a preferred embodiment, the device includes a motor having a motor axis, and the light refracting member is arranged on the motor axis connected to the motor. In another embodiment, the light refracting member is a mirror. In yet another embodiment, the light refracting member is a prism.

In accordance with another embodiment of the device of the present invention, the device includes a light analysis unit optically connected to the telescopic member. Preferably, the light analysis unit comprises a spectrometer.

In accordance with another embodiment of the device of the present invention, the telescopic member comprises a light focusing member adapted to focus light that enters the telescopic member and an opening adapted to direct the focused light out from the telescopic member. Preferably, the light focusing member is a lens. In another embodiment, the light focusing member is a mirror.

The present invention concerns a method for measuring emissions of gaseous substances to the atmosphere using scattered sunlight spectroscopy and an optical measuring device, said device comprising a telescopic member defining a field-of-view (FOV) of the device, and a scanning arrangement allowing a controlled variation of the direction of the field-of-view (FOV) in such a way that the field-of-view (FOV) is capable of scanning a certain layer (12, 22) of the atmosphere during operation of the device. The inventive method is characterized in that it comprises the step of scanning a scanning layer that has the form of, at least a part of, a cone having its apex positioned at the device and having a cone angle $\beta$.

Such a scanning layer is capable of being directed towards an emission source and partly surrounding the source resulting in several advantageous effects. One advantage is that it increases the wind direction interval within which a reliable measurement can be performed. A consequence of this is that a wider range of wind directions can be covered by a single instrument, or alternatively that a smaller number of stationary measuring devices are required to cover all possible wind directions around an emission source. Another advantage is that the distance between the measuring device and the location where an emission plume is scanned is decreased which improves the reliability of the measurement as the previously described scattering effects are reduced. This is of particular importance when the wind direction deviates considerably from a direction right above the place where the measuring device is positioned.

In a preferred embodiment of the inventive method, the cone angle $\beta$ is $\leq 80°$ and $\geq 20°$. Preferably, the cone angle $\beta$ is in the interval 40-70°.

The invention also concerns an optical measuring device for measuring emissions of gaseous substances to the atmosphere using scattered sunlight spectroscopy, said device comprising a telescopic member defining a field-of-view (FOV) of the device, and a scanning arrangement allowing a controlled variation of the direction of the field-of-view (FOV) in such a way that the field-of-view (FOV) is capable of scanning a certain layer of the atmosphere during operation of the device. In the inventive device, the scanning arrangement is adapted to form a scanning layer that has the form of, at least a part of, a cone having its apex positioned at the device and having a cone angle $\beta$.

In a preferred embodiment of the inventive device, the scanning arrangement comprises a light refracting member arranged to deflect the field-of-view (FOV) by directing a portion of incoming sunlight towards the telescopic member. Such a design makes it possible to control the light refracting member, instead of the telescopic member, as to vary the direction of the FOV, which is less complicated. Preferably, the light refracting member is arranged in such a way that the non-deflected FOV and the deflected FOV forms the angle $\beta$. No further parts are thus needed for achieving this angle.

In a further preferred embodiment of the inventive device, the light refracting member is rotatably arranged in relation to the telescopic member in such a way that rotation of the light refracting member allows the field-of-view (FOV) to scan the scanning layer. Preferably, the light refracting member is arranged on a motor axis connected to a motor.

BRIEF DESCRIPTION OF THE DRAWINGS

In the description of the present invention set forth in the following detailed description, reference is made to the following figures, in which.

DETAILED DESCRIPTION

Figure 1:
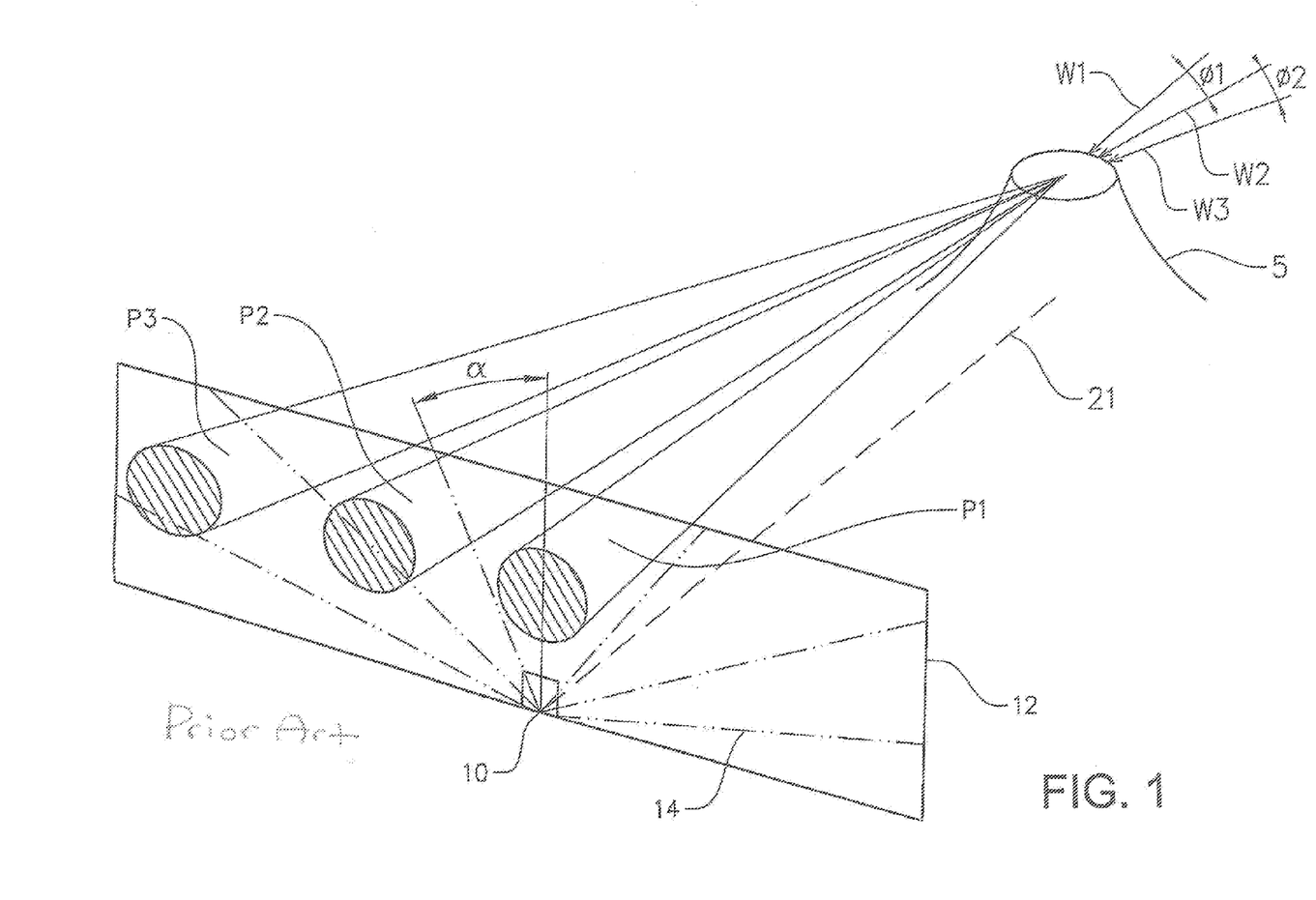
FIG. 1 is a front, perspective, schematic view of a principal illustration of the use of a prior art optical measuring device.
Figure 2:
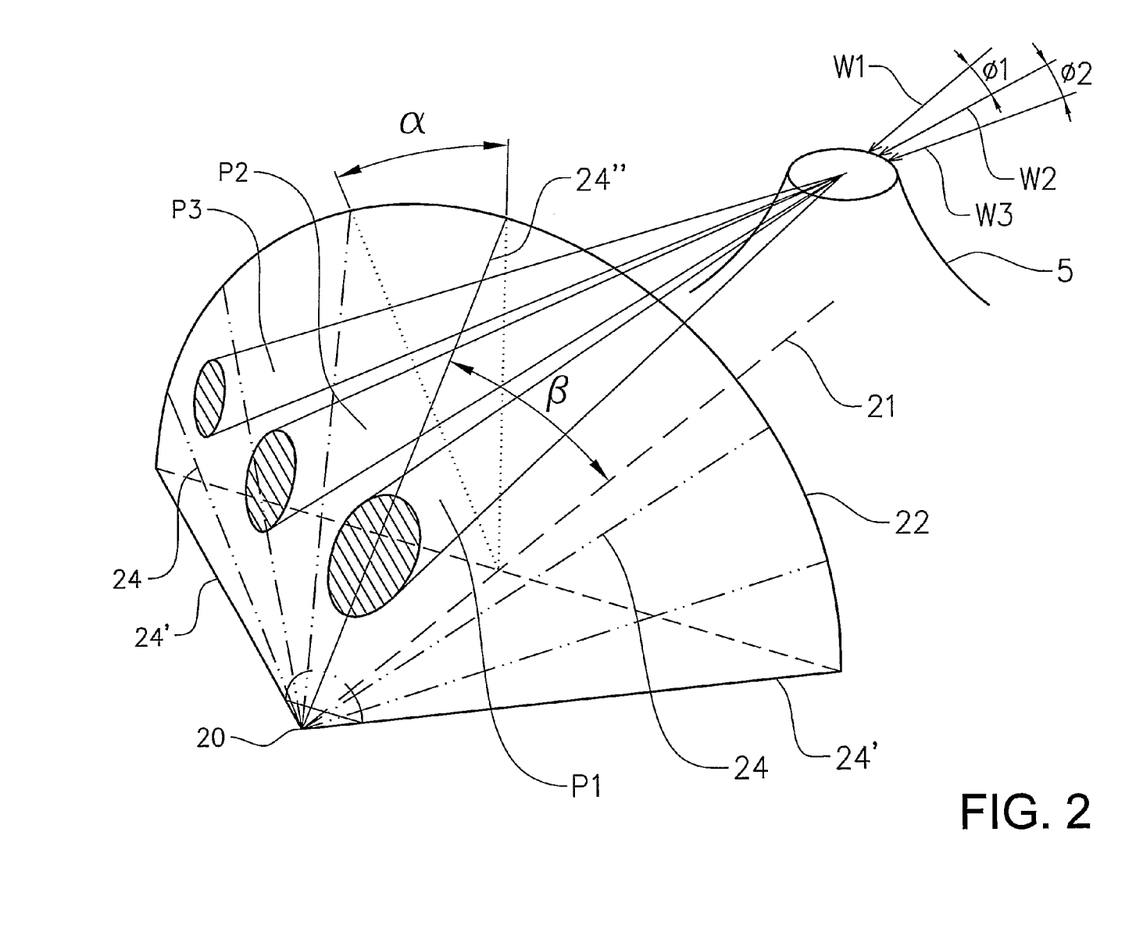
FIG. 2 is a front, perspective, schematic view of a principal illustration of the use of the method and device of the present invention.

FIGS. 1 and 2 show a 3-d representation of the measurement strategies for the prior art and the present invention, respectively. FIG. 1 gives a principal illustration of the use of a prior art optical measuring device 10 in the form of a scanning mini-DOAS in measurements of a gas emission from a source in the form of a volcano 5. In particular, FIG. 1 illustrates the effect of different plume directions relative to the location of the measuring device 10. Three different plumes P1, P2 and P3 represent three different wind directions W1, W2 and W3. The first wind direction W1 is directed from the gas emission source 5 towards the measuring device 10 resulting in that the corresponding plume P1 passes right above the measuring device 10. The second wind direction W2, and thus the direction of the second plume P2, exhibit an angle $\Phi_1$ relative to the direction of W1 and P1 such that the second plume P2 passes above the measuring device 10 somewhat at the side. The third wind direction W3, and thus the direction of the third plume P3, exhibit an angle $\Phi_1+\Phi_2$ relative to the direction of W1 and P1 such that the third plume P3 passes above the measuring device 10 further at the side.

FIG. 1 further shows a scanning layer 12 which in this case has the form of a vertical plane, and which will be further described below.

As described further above the prior art scanning mini-DOAS scans the field-of view (FOV) of the instrument step by step from horizon to horizon. In each scanning position, i.e. in each step, the FOV defines a more or less slanting column extending through the atmosphere which columns contain the air to be measured. A number of such columns are indicated by lines 14 in FIG. 1. Each of these lines 14 represents a solid angle defined by the FOV of the instrument. For clarity reasons these lines 14 have been given a certain length although the columns or FOV's strictly speaking have an infinite length. All the columns 14 taken together define the scanning layer 12 which in FIG. 1 has the form of a vertical plane. Indicated in FIG. 1 is also a scan step angle α. When the FOV is in a zenithal position, i.e. when it is directed vertically α is 0° and when it is directed horizontally α is either 90° or −90°. FIG. 1 further shows sectional views of the plumes P1, P2 and P3 taken along the scanning layer 12.

FIG. 2 shows the principles of the present invention in a situation similar to what is shown for the conventional equipment in FIG. 1. In the example shown in FIG. 2 the inventive measuring device 20 is arranged such that in each scanning position the FOV defines a column (indicated by lines 24) that exhibits an angle β of 45° relative to a direction defined by an imaginary, horizontal line 21 drawn between the measuring device 20 and the emission source 5. This results in a curved scanning layer 22 that has the shape of an upper half of a horizontal cone having its axis of symmetry 21 corresponding to the imaginary line 21, having its apex positioned at the measuring device 20 and having a cone angle β=45°. This means that the cone, and thus the scanning layer 22, has an opening angle in the horizontal plane, i.e. the angle between the lowest, substantially horizontal, columns 24', that is 2·β=90° and a vertical opening angle, i.e. the angle between the most vertical column 24" and ground, that is β=45°. The scan step angle α has the same meaning in FIG. 2 as in FIG. 1; when the FOV is in its most vertical position, i.e. when it is directed as indicated by line 24", α is 0° and when it is directed horizontally, i.e. when it is directed as indicated by lines 24', α is either 90° or −90°. FIG. 2 further shows sectional views of the plumes P1, P2 and P3 taken along the scanning layer 22.

In contrast to the planar scanning layer 12 shown in FIG. 1, the scanning layer 22 of the present invention exemplified in FIG. 2 has an opening angle in the horizontal plane that is less than 180° (which it will have as long as the cone angle β is less then 90°). For this reason the scanning layer 22 becomes funnel-shaped which make it possible to direct the scanning layer 22 towards the emission source 5 and thereby letting the scanning layer 22 at least partly surround the source 5. This has some advantages which will be described further below.

Figure 3:
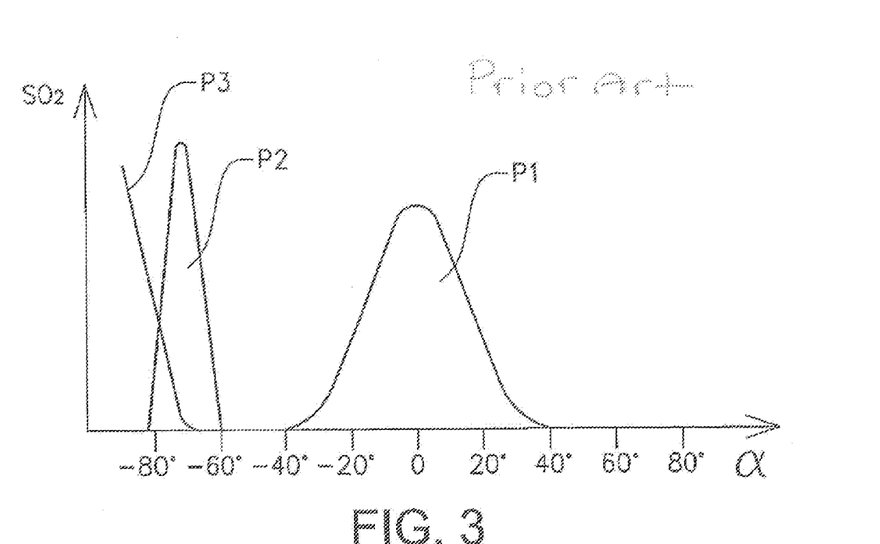
FIG. 3 is a graphical representation of an example of the measurement results obtained with the prior art device according to FIG. 1.

FIG. 3 shows a principal absorption column representation of a derived content of a gaseous substance, in this example $SO_2$, in a particular direction of the FOV, i.e. in a particular air column, as a function of scan step angle α obtained with a prior art measuring device 10 in a measurement corresponding to the conditions of FIG. 1. As plume P1 passes straight above the measuring device 10 at α=0° the maximum slant column for P1 is positioned in the middle of the scan with background values on each side of the peak resulting in that a good measurement of the integrated mass in plume P1 can be performed. Regarding plume P2 a reasonably good measurement can still be performed as a background measurement is obtained below the plume at about −80°. Regarding plume P3 no reliable measurement can be performed as only a part of the plume peak is registered, i.e. the FOV is still directed towards the plume at the lowest scan angle which in this example is −80°. A change of the wind direction from W1 to W3, i.e. a change of $\Phi_1+\Phi_2$ degrees, thus makes the measurement unreliable. Considering the peak of P2 in FIG. 3 to be sufficiently defined for an acceptable reliability of the measurement the acceptable change in wind direction for a reliable measurement with the prior art mini-DOAS is thus +/−$\Phi_1$ if the measuring device 10 initially is placed right below the plume.

Figure 4:
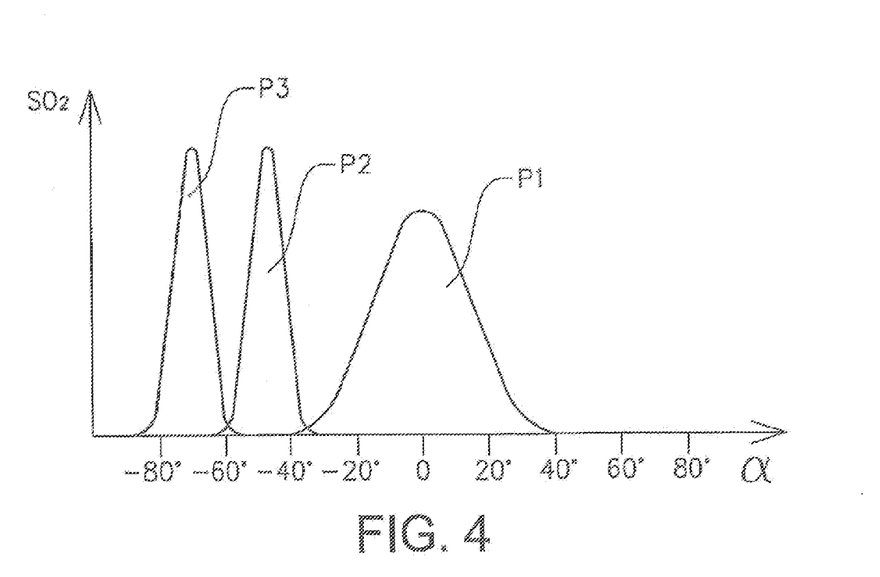
FIG. 4 is a graphical representation of an example of the measurement results obtained with the inventive method and device according to FIG. 2.

As a comparison to FIG. 3, FIG. 4 shows a similar principal absorption column representation as shown in FIG. 3 but obtained with an inventive measuring device 20 in a measurement corresponding to the conditions of FIG. 2. Plume P1 passes straight towards and above the inventive measuring device 20 such that at α=0° the maximum slant column for P1 is, in similarity with FIG. 3, positioned in the middle of the scan with background values on each side of the peak resulting in that a good measurement of the integrated mass in plume P1 can be performed. Regarding plume P2 a good measurement can be performed as a background measurement is obtained below the plume at about −60°. In contrast to FIG. 3 where only a part of the plume peak of P3 is registered, in this case also plume P3 can be reasonably well measured as a background measurement is obtained below the plume at about −80°. Thus, a change of the wind direction from W1 to W3, i.e. a change of $\Phi_1+\Phi_2$ degrees, does not make the measurement unreliable. Considering the peak of P3 in FIG. 4 to be sufficiently defined for an acceptable reliability of the measurement the acceptable change in wind direction for a reliable measurement with the inventive measuring device 20 is thus +/−($\Phi_1+\Phi_2$) if the measuring device 20 initially is placed right below the plume.

Due to topographical and atmospheric radiation limitations, there is normally a lower limit in scan angle (α) below which no reliable slant column density can be derived. Under good conditions this angle is typically 80°-85°.

As mentioned above, the inventive scanning layer 22 is funnel-shaped which makes it capable of partly surrounding the source 5. This leads to at least two major advantages. Firstly, it increases the wind direction interval within which a reliable measurement can be performed. This is illustrated in FIGS. 2 and 4, as compared to FIGS. 1 and 3, showing that also the third plume P3 now can be measured reliably since background data can be obtained also for scan step angles α below the plume P3. This is a major improvement compared to the measurement with the conventional equipment. A consequence of this is that a wider range of wind directions can be covered by a single instrument, or alternatively that a smaller number of stationary measuring devices 20 are required to cover all possible wind directions around an emission source 5. Secondly, the distance between the measuring device 20 and the location where the plume is scanned is decreased which improves the reliability of the measurement as the previously described scattering effects are reduced. This is illustrated in table 1 where the distance between instrument and gas plume is shown as a function of wind direction deviation Φ for the two different measurement strategies, using as an example a typical volcano with a height of 1 km, located 3 km away and the instrument having a cone angle β=45°.

Table 1 shows that the distance from the measuring device to the gas plume, for wind direction deviations Φ of more than around 30°, is considerably shortened with the scanning layer 22 according to the invention compared to the scanning layer 12 according to conventional technique. It should be noted that for Φ>80°, the conventional technique starts to get useless, while the inventive technique still give useful data even beyond Φ>100°, thus making possible the total surrounding of a source using only two measuring systems (see FIG. 5). For wind direction deviations Φ of less than around 30°, corresponding to the plume center passing close to zenith, the present invention gives a slightly longer distance between instrument and plume. However, this distance is here still relatively short so this minor disadvantage is well compensated by the strong advantage at larger, more critical, wind direction deviations.

TABLE 1

Distance from instrument to the point where the measurement intersects the gas plume, for different plume direction deviations. Plume height 1 km, distance to volcano 3 km, β = 45°.

| Wind direction deviation Φ (degrees) | Conventional geometry scan layer 12 (km) | Invention geometry scan layer 22 (km) |
|---|---|---|
| 0 | 1.00 | 1.41 |
| 10 | 1.13 | 1.50 |
| 20 | 1.48 | 1.69 |
| 30 | 2.00 | 1.94 |
| 40 | 2.72 | 2.21 |
| 50 | 3.72 | 2.51 |
| 60 | 5.34 | 2.83 |
| 70 | 8.32 | 3.20 |
| 80 | 17.37 | 3.65 |
| 90 | ∞ | 4.26 |
| 100 | N/A | 5.13 |
| 110 | N/A | 6.59 |

Another reason for the improvement of the measurement reliability with the new scanning geometry is that, ideally for the flux measurement, and even more important for the plume-speed measurement, the scanning should be made in a plane relatively close to perpendicular to the plume propagation. In table 2 is shown the angle between the horizontal projection of the direction of the instruments FOV and the plume propagation direction, for different plume propagation directions Φ. As the wind direction is deviating more and more from 0, the angle under which the plume is scanned is deviating more and more from perpendicular to the plume propagation. With the inventive scanning layer 22 this effect is strongly suppressed. For wind direction deviations Φ of less than around 60°, the deviation from the ideal perpendicular traverse is still less than 20°, and even for Φ=90° the deviation is not more than 47° with the inventive device.

TABLE 2

Angle between the horizontal projection of the direction of the instruments FOV and the plume propagation direction, for different plume direction deviations. Plume height 1 km, distance to volcano 3 km, β = 45°.

| Wind direction deviation Φ (degrees) | Conventional geometry scan layer 12 (degrees) | Invention geometry scan layer 22 (degrees) |
|---|---|---|
| 0 | 90 | 90 |
| 10 | 100 | 82 |
| 20 | 110 | 81 |
| 30 | 120 | 86 |
| 40 | 130 | 93 |
| 50 | 140 | 100 |
| 60 | 150 | 109 |
| 70 | 160 | 118 |
| 80 | 170 | 127 |
| 90 | N/A | 137 |
| 100 | N/A | 146 |
| 110 | N/A | 155 |

In principal, these improvements gradually increase as the cone angle β is reduced from 90°. However, the effect is not likely to be significant when β>80°. For geometrical reasons it is likely that the error in the flux calculations increases when the cone angle β gets too small. Nevertheless, as a low value of β makes it possible to completely surround the source with fewer instruments, low values of β, less than 45°, may still be attractive in some applications where a detection of a dramatic change in emission is interesting, e.g. the opening of a conduit system of a volcano. An example of a surrounding arrangement is given in FIG. 5. Here two systems are set up around a volcano at a distance of 2 km. The volcano is 1 km high. The cone angle β was 45° and the scan angle α was ranging between ±70° with 5° steps. As can be seen the two scanning systems puts up an effective "grid" facilitating the detection of gas emission in all possible directions, providing a cost effective way to detect dramatic changes in the gas emission.

Figure 5:
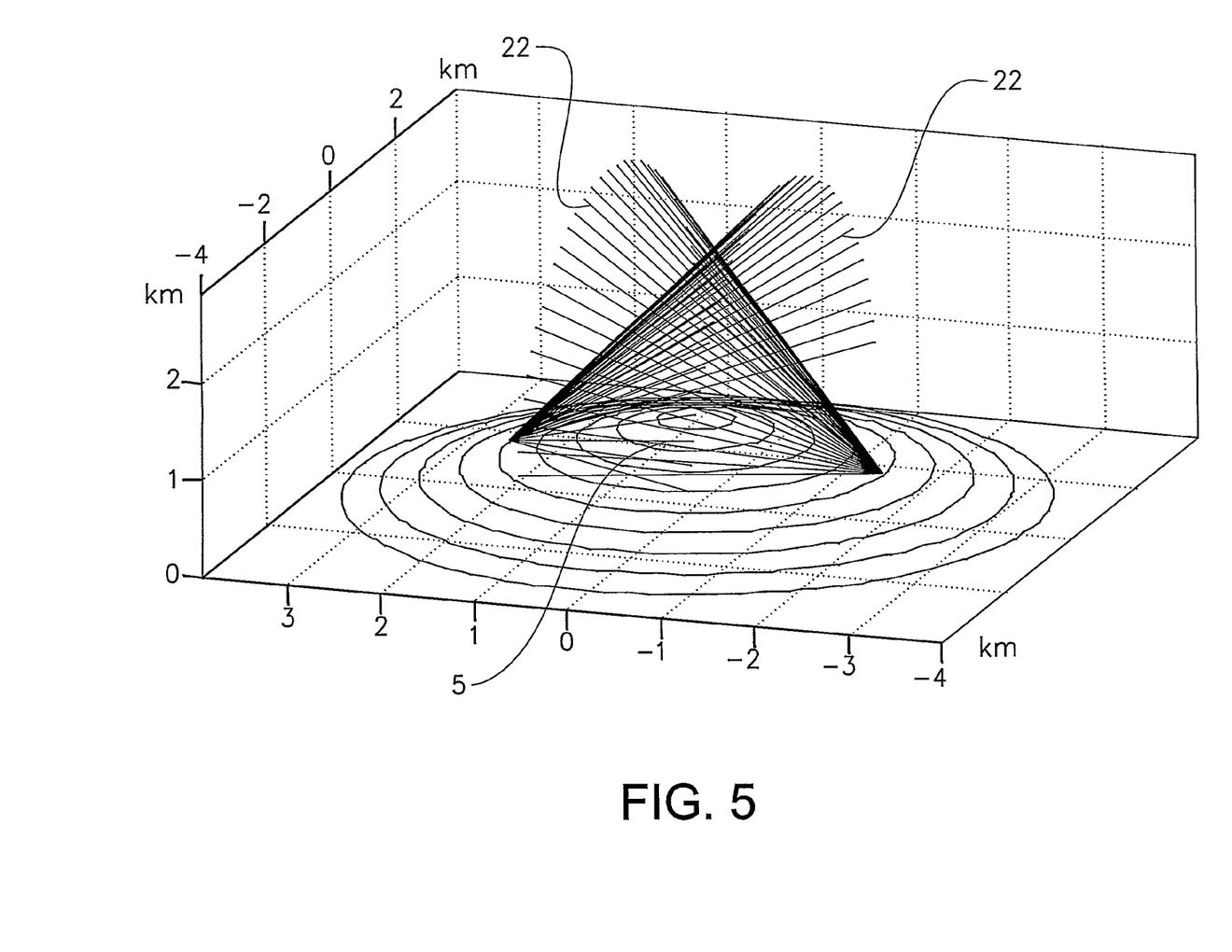
FIG. 5 is a schematic, representational view of an example of how the present invention can be used to surround an emission source.
Figure 6:
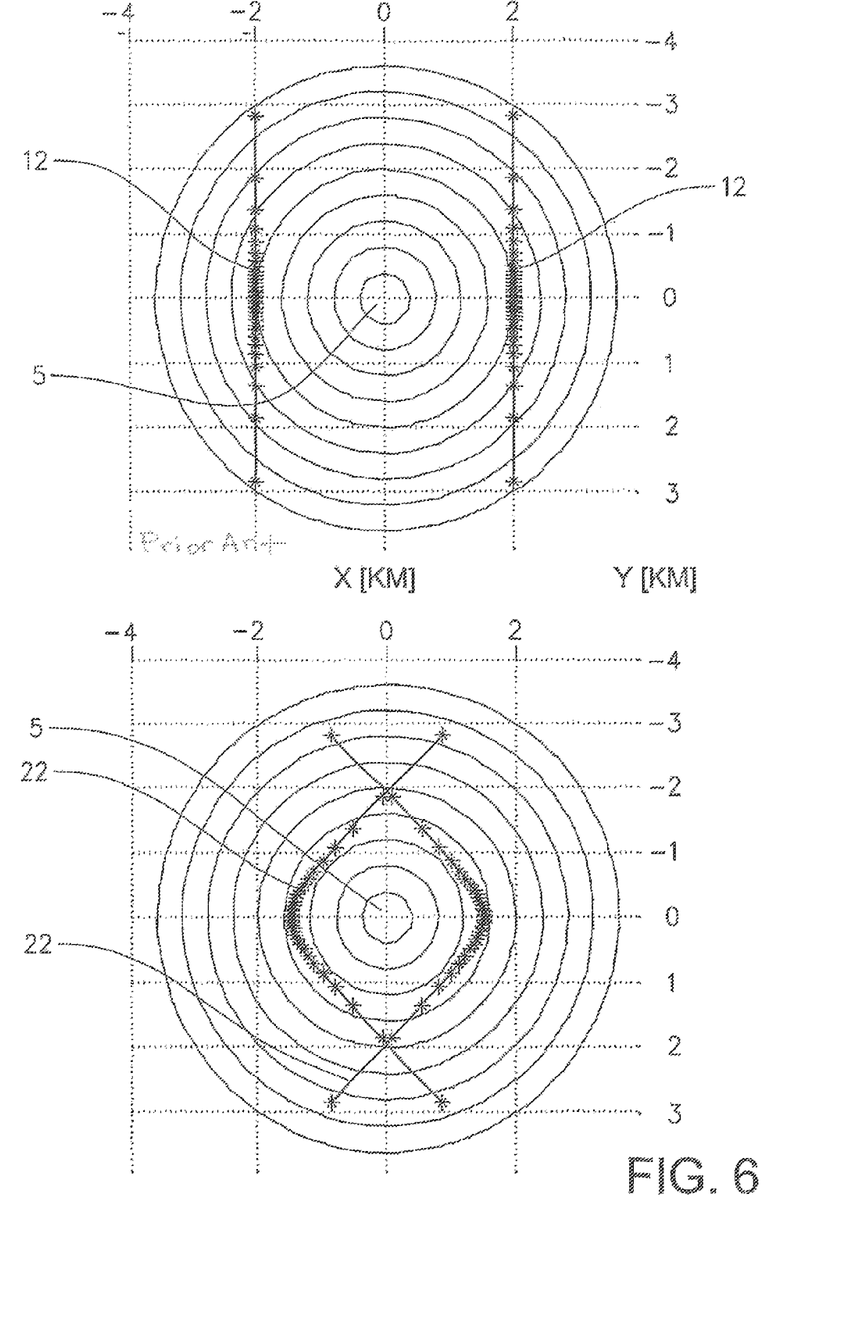
FIG. 6 is a top, schematic, representational view of the example of FIG. 5 as seen from above, together with a similar view of a prior art device.

The lower part of FIG. 6 shows a top view of FIG. 5 where the intersection between the FOV columns 24, i.e. the conical scanning layer 22, and the plume plane at 1 km height are indicated with crosses. As a comparison, the upper part of FIG. 6 also shows a top view of two conventional measuring devices 10 located in the same positions as the inventive devices in FIG. 5 and lower part of FIG. 6. It is clear that the two parallel, planar, vertical scanning layers 12 formed by the conventional devices do not cover varying wind directions from the volcano 5 as well as the inventive devices.

Figure 7:
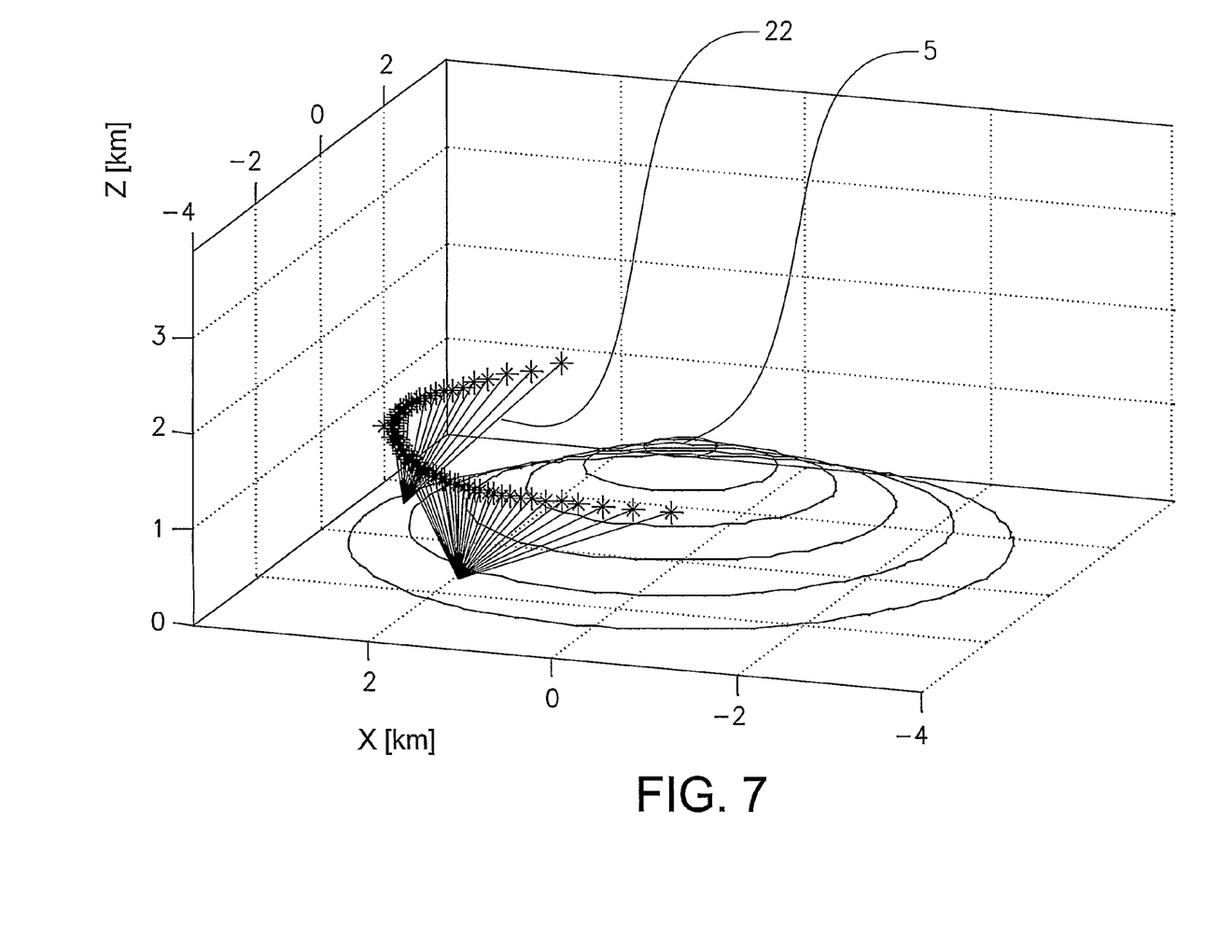
FIG. 7 shows another example of the use of the invention.

In a variant of the inventive cone-shaped scanning layer 22 described above the axis of symmetry of the cone is no longer horizontal but instead have an inclination δ. A special case of this embodiment is when δ=90°−β. Then the scanning direction will point towards zenith when α=0. This may be advantageous in some applications, e.g. if the earlier described dual-beam method is used for plume speed measurements. A further special case of this embodiment is if the cone inclination δ equals the inclination angle from the instrument to the source. In this special case the cone axis point towards the source. This has the additional advantage that the scan makes an almost vertical intersection of the plume when α is around ±90°. It also makes the scan perpendicular to the plume for low scan angles α. This reduces the error in the flux calculation caused by geometrical inaccuracies as well as improves the possibility to make successful measurements using the dual-beam plume speed measurement approach. An example of such a special embodiment set up for measurements of emission from a volcano using two measurement systems is shown in FIG. 7. Here δ=90°−β=30°=inclination angle between instrument and volcano.

Figure 8:
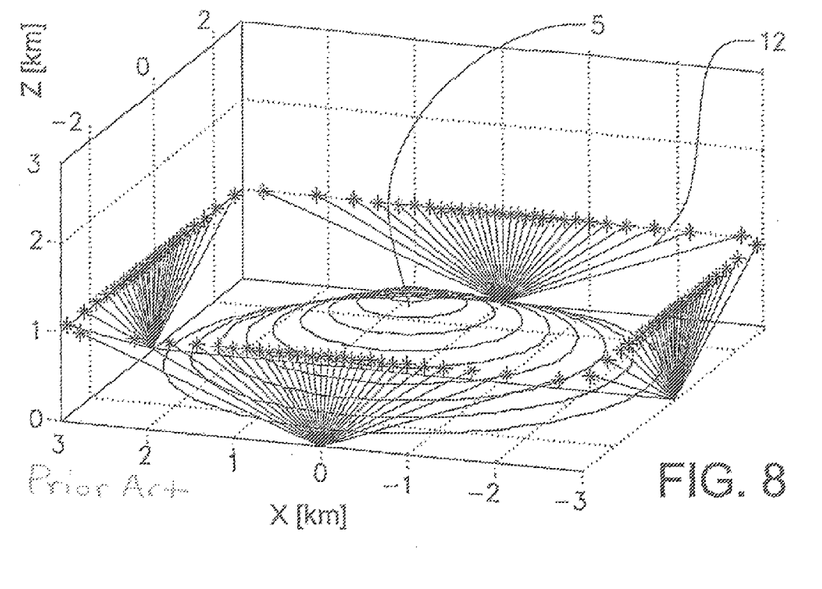
FIG. 8 is a schematic, representational view of the use of four prior art devices arranged around an emission source.
Figure 9:
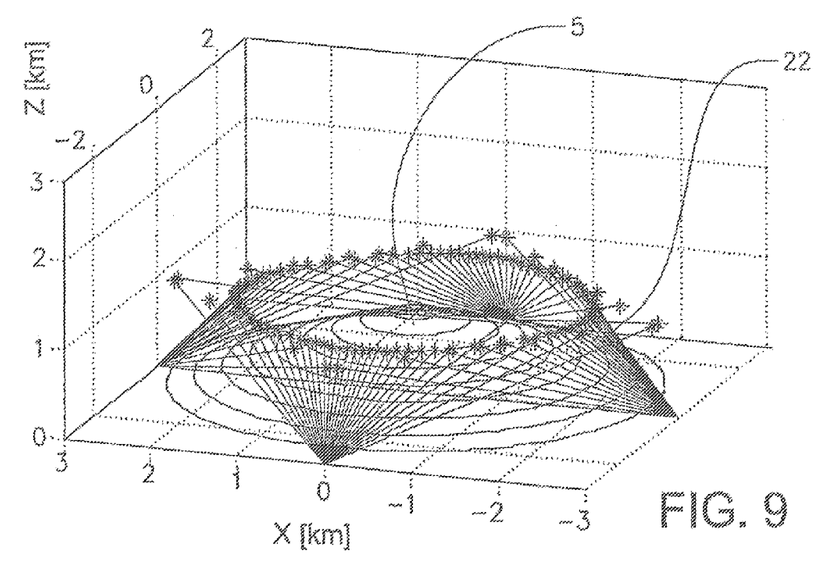
FIG. 9 is a schematic, representational view of the use of four devices of the present invention arranged around an emission source.

Further advantages of the inventive scanning layer are that it improves the possibility to make 2-d representations of the concentration field of the gas plume, using two or more measuring devices. For calculations of the flux from the data obtained with the instrument a knowledge of the height of the gas plume, or ideally the concentration distribution in the plane of the scanning, is necessary. This is needed for three reasons; Firstly, because the wind speed usually shows a strong gradient with height. Thus knowledge of the plume height is important in order to be able to establish the correct plume speed to calculate the mass-transport. Secondly, when calculating the total number of molecules in a cross-section of the plume each scanning direction represents a certain scanned area along the cone surface. This area increases linearly with the distance from the instrument. Thus, information about the plume height, and ideally also the distribution of the gas concentrations along the scanned cone surface, is important to obtain a correct number of molecules integrated over the scanned area of the plume. Finally information of the plume height is also necessary if the earlier described dual-beam method to derive plume speed is used. Information about the geographical distribution of the gas over the scanned area can be obtained from modelling, e.g. calculation of the expected plume lift, and using an appropriate dispersion model. Alternatively the distribution of the gas concentration over the scanned cone surface may be measured using two or more instruments scanning the plume from different directions, and making a tomographic reconstruction of the concentration field. This technique is relatively straightforward when the two systems are scanning in the same plane. When several systems are installed around a source a major reason for doing so is, however, to be able to cover varying wind directions. To maximize the coverage of different wind directions a more optimal setup is to distribute the measuring devices around the source. A disadvantage with such a setup when using the conventional technique is that the two systems now no longer scan the plume in the same geographical plane, and a tomographic reconstruction of the concentration field gets more complicated and less accurate. With the cone scanning method, choosing appropriate scanning parameters, a higher degree of overlap may be obtained, while also improving the coverage of varying wind directions. It can be shown that at the altitude where the plume intersection is expected, the overlap between the scans from the two instruments is almost perfect. A more extreme demonstration of this advantage, surrounding a volcano with four systems, is shown in FIGS. 8 and 9. Here the four systems in the conventional configuration (see FIG. 8) are scanning orthogonal to each other, with no overlap at all, while the inventive configuration (see FIG. 9) still shows an almost perfect overlap.

Figure 10:
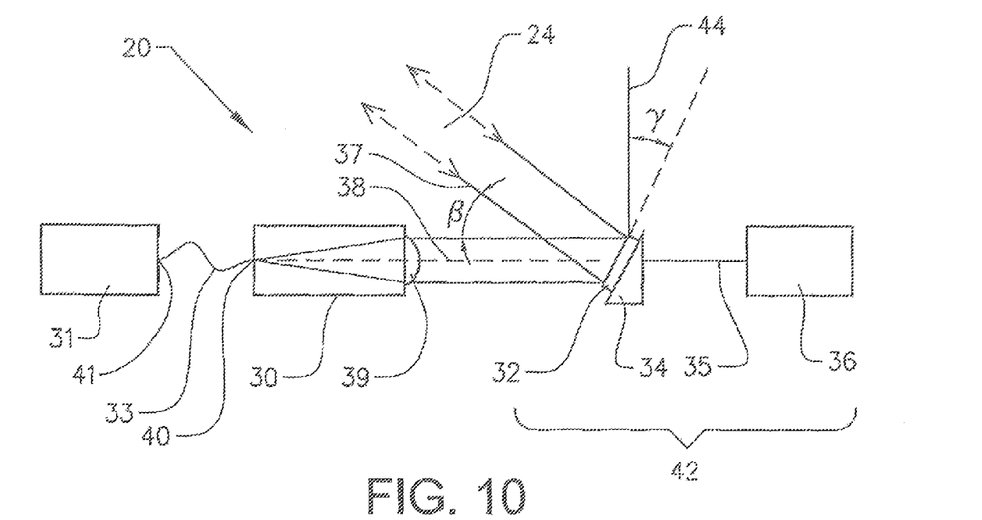
FIG. 10 is a top, elevational, schematic view of a preferred embodiment of the optical measuring device of the present invention.

FIG. 10 shows a preferred embodiment of an optical measuring device 20 according to the invention. The device 20 comprises a telescopic member 30 provided with a lens 39 and a focal point 40 at which an optical fiber 33 is attached as to optically connect the telescopic member 30 to a spectrometer 31 via its entrance slit 41. The telescopic member 30 defines an optical axis 38 and a field-of-view (FOV) 24 directed towards a scanning arrangement 42. The scanning arrangement 42 comprises a computer-controlled stepper-motor 36 that, via a motor axis 35, is connected to a mirror 32 mounted onto a supporting member 34, wherein the mirror 32 faces the telescopic member 30 as to establish an optical connection. The mirror 32 is arranged so that the direction of the FOV 24 forms an angle $\beta$ with the optical axis 38. A certain portion of scattered sunlight 37 falling within the FOV 24 into the mirror 32 will thus be directed towards the telescopic member 30 and thus to the spectrometer 31. When the motor axis 35, and thus the mirror 32, is rotated the FOV 24 of the telescopic member 30 defines the scanning layer 22 (see FIG. 2) in the atmosphere which layer 22 forms a part of a cone with an axis of symmetry along the optical axis of the telescopic member 30, a top at the mirror 32 and a cone angle $\beta$.

If the measuring device 20 is used in a horizontal direction, i.e. if the optical axis 38 and the co-axially arranged motor axis 35 are horizontal, the symmetry axis of the scanning cone will also be horizontal. As mentioned above, the measuring device 20 can however be tilted vertically with an angle $\delta$, resulting in that the symmetry axis of the scanning cone gets a vertical inclination $\delta$.

From geometrical laws it follows that the mirror 32 exhibits an angle $\gamma$ with a plane 44 perpendicular to the motor axis 35 and the optical axis 38 where $\gamma=\beta/2$. It also follows that the mirror 32 exhibits an angle with the axes 35, 38 that is equal to $(90-\gamma)°$. In this example $\beta=45°$ which means that $\gamma=22.5°$.

An instrument based on the above mentioned ideas has been built and its performance was tested in a field test on the gas-plume from the active'volcano Popocatepetl in Mexico. The measuring device 20 used in the field test consists of a small telescope 30 (quartz lens, focal length=50 mm, diameter=20 mm, field of view approximately 0.4°) coupled to a quartz fiber bundle 33, which transmits the light 37 into a commercial miniature fiber optic spectrometer 31 (OceanOptics Inc., USB2000). The telescope 30 is optically connected to a scanning device 42 consisting of a mirror 32 attached to a computer-controlled stepper-motor 36, providing a means to scan the field-of view 24 of the instrument over 180°, i.e. the motor axis is rotated 180°. The mirror 32 was positioned such that an angle $\beta$ was formed with the optical axis 38 as shown in FIG. 10 as to form a cone shaped scanning layer 22. In this particular experiment the angle $\beta$ was 45°. Typically a seconds integration time was used, with 7.5° angular resolution, providing a full emission measurement every 4 minutes. The 2 m long quartz fiber bundle 33 consisted of four individual 200 µm core diameter fibers, arranged in rectangular configuration in the focal point 40 of the telescope 30 and a linear arrangement at the spectrometer entrance slit 41. A Hoya U330 filter blocked the visible light >400 nm to reduce the stray light in the spectrometer. The USB2000 spectrometer 31 used was a crossed Czerny-Turner arrangement (1/f=2.2, UV grating 2400 grooves/mm) with a CCD detector (2048 elements at 12.5 µm centre–centre spacing) coupled to a 12-bit ADC, which connects to a PC via a serial RS232 interface. The quartz fiber 33 transmits the light to the entrance slit 41 (width 50 µm), which guarantees a spectral resolution of 0.7 nm. The wavelength region observed by the detector was set from 245 nm to 380 nm. The wavelength to pixel mapping as well as the instrumental line shape was determined by taking a spectrum of a low-pressure mercury emission lamp. The entire system (notebook PC, spectrometer and stepper motor) operates on 12 V for about 24 hours from a standard car battery. The known Differential Optical Absorption Spectroscopy (DOAS) technique was applied to identify and quantify the atmospheric trace gases by their specific narrow band absorption features in the UV and visible spectral regions.

The fundamental equation of absorption spectroscopy is the Beer-Lambert's Law. It describes the decrease of light intensity while light passes matter.

$$I(\lambda,L)=I_0(\lambda)*e^{-S*\sigma}$$

$I_0(\lambda)$—light intensity outside the gas layer to be measured
$I(\lambda, L)$—light intensity after passing the gas layer to be measured
$\lambda$—wavelength of the radiation
$c(l)$—concentration of the trace gas as function of the position l along the light path σ(λ, T)—trace gas absorption cross section
T—temperature
L—length of light path $$S = \int_0^L c(l)\,dl\,( = c*L, \text{ if } c = \text{const.}) -$$

Definition of slant column density (SCD)

SCD were directly determined here as results of the measurements. Fluxes can however be calculated using further estimates. Automatic data acquisition, real time spectral evaluation and flux calculations was performed by a home-made C-program running on a notebook computer under the WINDOWS operating system.

Figure 11:
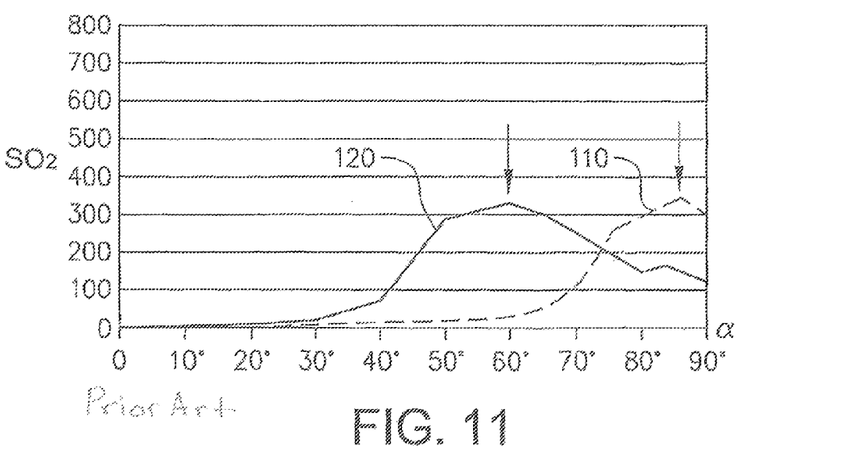
FIG. 11 is a graphical representation of the present invention actual measurement results obtained with a prior art device and with the device of the present invention.

FIG. 11 shows some results from the testing of the inventive measuring device 20. For comparison, tests were also made with a conventional instrument, using a flat vertical scanning plane 12 passing zenith, operated in parallel from the same location. FIG. 11 shows the results from the different devices in the form of a representation of $SO_2$ in a particular air column/FOV-direction 14, 24 as a function of scan step angle α as given by the extent of rotation of the motor axis 35. Note that in contrast to FIGS. 3 and 4, the x-axis of FIG. 11 starts at 0°. Thus only "half" scans was performed, starting at zenith going down to one horizon. Over a time period of 76 minutes 22 simultaneous scans was performed and the averaged results are shown. The averaged results obtained with the inventive measuring device 20 are given by solid lines 120 and the results obtained with the conventional equipment are given by dashed lines 110. The approximate centre position of each peak is indicated by arrows. At the time of the experiment the wind direction was such that the volcano plume passed the measuring device at some distance at the side, in similarity with plume P3 in FIGS. 1 and 2. FIG. 11 clearly shows that the peak recorded with the inventive measuring device is positioned sufficiently far away from the end of the scan allowing a reliable measurement. In contrast, the peak recorded with the conventional equipment is too close to the end of the scan to allow for a reliable measurement.

The present invention is not limited by the embodiments described above but can be modified in various ways within the scope of the claims. For instance, a variation of the direction of the field-of-view (FOV) can be achieved by a computer controlled variation of the position of the telescopic member 30. Alternatively, a computer controlled mirror could be used instead of mounting the mirror 32 to a rotatable motor axis 35.

Moreover, the spectrometer 31 may be replaced by another light analysis unit by which the slant column density of a gas or aerosol may be determined. In some applications it may for instance be sufficient to be able to detect a certain, narrow wavelength interval.

Further, a mirror could be used instead of the lens 39 as light focusing member, and a prism could be used instead of the mirror 32 as light refracting member. The optical fiber is optional; the spectrometer 31 or other light analysis unit may be connected directly to the telescopic member 30.

It should also be noted that it is not necessary that the measurement is carried out stepwise; the scan angle α can be varied more or less continuously as to let the FOV 24 continuously scan the scanning layer 22.

In a preferred variant of the inventive device the mirror 32 is adjustable such that the angle β becomes adjustable.

The angles can vary within their defined ranges; $-180° \leq \alpha \leq 180°$, $0° \leq \beta < 90°$, $-90° \leq \delta \leq 90°$. Although the inclination angle δ will be $\geq 0°$ in most applications, i.e. the cone is either horizontal or has its wider part pointing upwards as to point towards a source positioned at a higher level, it is possible to use a negative δ, i.e. where the cone has its wider part pointing downwards. It may also be noted that the horizontal pointing direction of the cone, i.e. the direction of the symmetry axis of the cone as projected onto the horizontal plane if the cone is inclined relative to this plane, does not necessarily have to be identical to the horizontal direction between instrument and source. For instance, if the view towards the source for topographical reasons is obstructed, one may "aim" with the cone at the side of the source.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for measuring emissions of gaseous substances to the atmosphere using scattered sunlight spectroscopy and an optical measuring device comprising
   a telescopic member defining a field-of-view of said optical measuring device,
   a scanner for controlling the variation of the direction of said field-of-view to scan a predetermined layer of the atmosphere, and
   a spectrometer for obtaining the spectra of scattered light, said method comprising
   scanning said field-of-view to scan said predetermined layer of the atmosphere in the form of at least a part of a cone having its apex positioned at said optical measuring device and having a cone angle β, and obtaining the spectra of scattered sunlight at different directions of said field of view during said scanning using said spectrometer.

2. The method according to claim 1, wherein said cone angle β is up to 80°.

3. The method according to claim 1, wherein said cone angle β is at least 20°.

4. A method according to claim 1, wherein said cone angle β is from 40 to 70°.

5. A method according to claim 1, wherein said cone has its axis of symmetry in a horizontal direction.

6. A method according to claim 1, wherein said cone has an axis of symmetry exhibiting an inclination angle (δ) relative to a horizontal plane.

7. A method according to claim 6, wherein said inclination angle (δ) is 90°-β.

8. An optical measuring device for measuring emissions of gaseous substances to the atmosphere using scattered sunlight spectroscopy, said device comprising
   a telescopic member defining a field-of-view of said measuring device,
   a scanner for controlling the variation of the direction of said field-of-view to scan a predetermined layer of the atmosphere, said scanner being adapted to scan said predetermined layer of the atmosphere in the form of at least a part of a cone having its apex positioned at said optical measuring device and having a cone angle β and a spectrometer capable of obtaining spectra of scattered sunlight at different directions of said field of view during the operation of said scanner.

9. The device according to claim 8, wherein said cone angle β is up to 80°.

10. The device according to claim 8, wherein said cone angle β is at least 20°.

11. The device according to claim 8, wherein said cone angle β is from 40 to 70°.

12. The device according to claim 8, wherein said scanner comprises a light refracting member arranged to deflect said field-of-view by directing a portion of incoming sunlight towards said telescopic member.

13. The device according to claim 12, wherein said light refracting member is arranged in such a way that the non-deflected field-of-view and the deflected field-of-view form the angle β.

14. The device according to claim 12, wherein said light refracting member is rotatably arranged in relation to said telescopic member whereby rotation of said light refracting member allows the field-of-view to scan said predetermined layer of the atmosphere.

15. The device according to claim 14, including a motor having a motor axis, and wherein said light refracting member is arranged on said motor axis connected to said motor.

16. The device according to claim 12, wherein said light refracting member is a mirror.

17. The device according to claim 12, wherein said light refracting member is a prism.

18. The device according to claim 8, wherein said telescopic member comprises a light focusing member adapted to focus light that enters said telescopic member and an opening adapted to direct the focused light out from said telescopic member.

19. The device according to claim 18, wherein said light focusing member is a lens.

20. The device according to claim 18, wherein said light focusing member is a mirror.

* * * * *

UNITED STATES PATENT AND TRADEMARK OFFICE
CERTIFICATE OF CORRECTION

PATENT NO.         : 8,035,813 B2
APPLICATION NO.    : 12/308548
DATED              : October 11, 2011
INVENTOR(S)        : Bo Galle Page 1 of 1

It is certified that error appears in the above-identified patent and that said Letters Patent is hereby corrected as shown below:

Column 7, line 40, delete "a" and insert therefor --α--.
Column 12, line 18, delete """.

Signed and Sealed this
Thirtieth Day of October, 2012

David J. Kappos
*Director of the United States Patent and Trademark Office*